(12) United States Patent
Miura et al.

(10) Patent No.: US 6,509,025 B2
(45) Date of Patent: Jan. 21, 2003

(54) METHOD OF PRODUCING AN IMPACT RESISTANT SOLID COSMETIC COMPOSITION

(75) Inventors: Yoshimasa Miura, Kanagawa (JP); Sadaki Takata, Kanagawa (JP); Kazuo Takahashi, Kanagawa (JP); Fukuji Suzuki, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 10/076,311

(22) Filed: Feb. 19, 2002

(65) Prior Publication Data

US 2002/0168390 A1 Nov. 14, 2002

Related U.S. Application Data

(63) Continuation-in-part of application No. 09/365,233, filed on Jul. 30, 1999, now abandoned.

(30) Foreign Application Priority Data

Jan. 31, 1998 (JP) ............................................. 10-229973

(51) Int. Cl.$^7$ ............................ A61K 7/00; A61K 7/42; A61K 7/035; A61K 31/74; A61K 9/14

(52) U.S. Cl. ........................... 424/401; 424/59; 424/69; 424/78.02; 424/78.03; 424/78.08; 424/489; 424/491; 424/497; 424/501

(58) Field of Search ........................... 424/401, 59, 69, 424/489, 491, 497, 501, 78.02, 78.03, 78.08

(56) References Cited

FOREIGN PATENT DOCUMENTS

GB           2303549           *  2/1997

* cited by examiner

*Primary Examiner*—Shelley A. Dodson
(74) *Attorney, Agent, or Firm*—Townsend & Banta

(57) ABSTRACT

A method is provided for producing an impact resistant solid cosmetic such as cheek rouge, powder, foundation and two way foundation by compacting powder materials into a dish mold. The powder materials are compression molded into a dish mold under a pressure of 200–300 kgf/cm$^2$ at a temperature of 10–30° C. The powder materials contain 0.1–50.0 wt % of a spherical organopolysiloxane elastomer having a JIS A hardness of 60–100, and a mean particle size of 0.1–200 μm. The cosmetic optionally contains 1.0–30.0 wt % of an oily ingredient.

18 Claims, No Drawings

METHOD OF PRODUCING AN IMPACT RESISTANT SOLID COSMETIC COMPOSITION

This application is a Continuation-In-Part application of parent U.S. patent application Ser. No. 09/365,233, filed Jul. 30, 1999, for which priority is claimed now abandoned.

FIELD OF THE INVENTION

The present invention relates to a cosmetic composition and, more particularly, to a method of preparing an impact resistant solid cosmetic composition. This method involves compression molding, into a dish mold, powder materials which contain spherical powders of organopolysiloxane elastomer.

BACKGROUND OF THE INVENTION

Conventionally, a spherical powder of an organopolysiloxane elastomer, having characteristic elasticity, has been developed as a powder for use in cosmetic compositions and has been incorporated into a variety of products. Such a powder exhibits favorable properties when incorporated into cosmetic compositions, i.e., the cosmetic composition containing such a powder exhibits good skin fittability and spreadability on the skin, imparts a light and smooth sensation when applied to the skin, has a soft-touch sensation, and does not irritate the skin (Japanese Patent Application Laid-Open (kokai) No. 2-243612 and Japanese Patent Publication (kokoku) Nos. 4-17162 and 4-66446).

However, when a spherical powder of organopolysiloxane elastomer is incorporated into a cosmetic composition in a large amount in order to fully realize favorable properties of the powder, the resultant solid cosmetic composition disadvantageously exhibits deteriorated strength against impact (hereinafter referred to as impact resistance).

SUMMARY OF THE INVENTION

In view of the foregoing, an object of the present invention is to provide a solid cosmetic composition having excellent strength against impact even when a spherical powder of organopolysiloxane elastomer is incorporated into the cosmetic composition in a large amount.

In order to overcome the drawbacks, the present inventors have conducted earnest studies on a spherical powder of organopolysiloxane elastomer, and have found that, among spherical powders of organopolysiloxane elastomer which have a mean particle size of 0.1–200 $\mu$m, a spherical powder of organopolysiloxane elastomer having a JIS A hardness of 50–100 does not impair the impact strength of a solid cosmetic composition even when the powder is incorporated into the cosmetic composition in a large amount, and provides a solid cosmetic composition having an excellent impact strength. The inventors have also found that a solid cosmetic composition containing a spherical powder of organopolysiloxane elastomer having a JIS A hardness of 50–100 exhibits excellent retention on the skin during use (hereinafter called "cosmetic retention") and has properties conventionally considered favorable, e.g., exhibiting good skin fittability and spreadability on the skin; imparting a light and smooth sensation when applied by rubbing (hereinafter referred to as light and smooth application sensation); and imparting no strange sensation or irritation to the skin. The present invention has been accomplished based on these findings.

Accordingly, in one aspect of the present invention, there is provided a solid cosmetic composition containing a spherical powder of organopolysiloxane elastomer having a JIS A hardness of 50–100 that has a mean particle size of 0.1–200 $\mu$m (hereinafter referred to as "the solid cosmetic composition of the present invention").

Preferably, the solid cosmetic composition contains the spherical powder of organopolysiloxane elastomer in an amount of 0.1–50.0 wt. % based on the entirety of the composition.

Particularly preferably, the solid cosmetic composition contains the spherical powder of organopolysiloxane elastomer having a JIS A hardness of 50–80.

As used herein, the term "mean particle size" refers to a value which. is obtained by measuring the diameters in a specific direction of particles under an optical microscope and dividing the sum of respective diameters of particles by the number of measured particles.

The term "JIS A hardness" refers to a hardness measured according to JIS K 6301 by use of the JIS A hardness meter.

The term "solid cosmetic composition" refers to a cosmetic composition which is solidified by compacting powder such as solid face powder, powdery foundation, two-way (i.e., usable with or without water) foundation, foundation usable with water, solid emulsified foundation, or solid cheek rouge.

In a first embodiment of the present invention concerning a method of producing an impact resistant solid cosmetic, a method is provided comprising compression molding into a dish mold powder materials comprising a spherical powder of organopolysiloxane elastomer having a JIS A hardness of 60–100, and a mean particle size of 0.1–200 mm, said elastomer constituting 0.1–50.0 wt % based on the entirety of the cosmetic.

In a second embodiment of the present invention concerning a method of producing an impact resistant solid cosmetic, a method is provided according to the first embodiment above, wherein the powder materials are compression molded at a pressure of between 200 kgf/cm$^2$ and 300 kgf/cm$^2$.

In a third embodiment of the present invention concerning a method of producing an impact resistant solid cosmetic, a method is provided according to the first embodiment above, wherein the powder materials are compression molded at a temperature of between 10° C. and 30° C.

In a fourth embodiment of the present invention concerning a method of producing an impact resistant solid cosmetic, a method is provided according to the first embodiment above, wherein the compacted powder materials in the compacted cosmetic constitute 70.0–99.0 wt %, based on the entirety of the cosmetic.

In a fifth embodiment of the present invention concerning a method of producing an impact resistant solid cosmetic, a method is provided according to the first embodiment above, wherein the impact resistant solid cosmetic further comprises an oily ingredient.

In a sixth embodiment of the present invention concerning a method of producing an impact resistant solid cosmetic, a method is provided according to the fifth embodiment above, wherein the amount of the oily ingredient is 1.0–30.0 wt %.

In a seventh embodiment of the present invention concerning a method of producing an impact resistant solid cosmetic, a method is provided according to the first embodiment above, wherein the organopolysiloxane elastomer has a JIS A hardness of 60–80.

In an eighth embodiment of the present invention concerning a method of producing an impact resistant solid cosmetic, a method is provided according to the first embodiment above, wherein the cosmetic is selected from the group consisting of face powder, powdery foundation, two way foundation, formulations usable with water, solid emulsified formulation, and cheek rouge.

In a ninth embodiment of the present invention concerning a method of producing an impact resistant solid cosmetic, a method is provided according to the first embodiment above, said method comprising compression molding into a dish mold a mixture comprising 70.0–99.0 wt % of said powder materials and 1.0–30.0 wt % of an oily ingredient, said powder materials comprising a spherical powder of organopolysiloxane elastomer having a JIS A hardness of 60–100, and a mean particle size of 0.1–200 mm, said elastomer constituting 0.1–50.0 wt % based on the entirety of the cosmetic.

In a tenth embodiment of the present invention concerning a method of producing an impact resistant solid cosmetic, a method is provided according to the ninth embodiment above, wherein the powder materials are compression molded at a pressure of between 200 kgf/cm$^2$ and 300 kgf/cm$^2$ at a temperature of between 10° C. and 30° C.

In an eleventh embodiment of the present invention concerning a method for producing an impact resistant solid cosmetic, a method is provided according to the ninth embodiment above, wherein the powder materials are compression molded at a pressure of between 200 kgf/cm$^2$ and 300 kgf/cm$^2$ at a temperature of between 10° C. and 30° C.

In an eleventh embodiment of the present invention concerning a method for producing an impact resistant solid cosmetic, a method is provided according to the first embodiment above, wherein the powder materials are compacted 1–3 times.

In a twelfth embodiment of the present invention concerning a method for producing an impact resistant solid cosmetic, a method is provided according to the eleventh embodiment above, wherein the powder materials are compacted at a temperature of about 20° C.±10° C.

In a thirteenth embodiment of the present invention concerning a method for producing an impact resistant solid cosmetic, a method is provided according to the twelfth embodiment above, wherein the powder materials are compacted under a pressure of 200–300 kgf/cm$^2$.

In a fourteenth embodiment of the present invention, an impact resistant solid cosmetic is provided which is produced by the method of the first embodiment above.

In a fifteenth embodiment of the present invention, an impact resistant solid cosmetic is provided which is produced by the method of the fifth embodiment above.

In a sixteenth embodiment of the present invention, an impact resistant solid cosmetic is provided which is produced by the method of the ninth embodiment above.

In a seventeenth embodiment of the present invention, an impact resistant solid cosmetic is provided which is produced by the method of the tenth embodiment above.

In an eighteenth embodiment of the present invention, an impact resistant solid cosmetic is provided which is produced by the method of the thirteenth embodiment above.

DETAILED DESCRIPTION OF PREFERRED EMBODIMENTS

Modes for carrying out the present invention is described.

The spherical powder of organopolysiloxane elastomer which is incorporated into the solid cosmetic composition of the present invention is composed of an organopolysiloxane elastomer having a JIS A hardness of 50–100, preferably 50–80. When the JIS A hardness is less than 50, the solid cosmetic composition containing the powder disadvantageously has poor strength against impact, whereas when the hardness is in excess of 100, cosmetic retention is disadvantageously deteriorated.

The spherical powder of organopolysiloxane elastomer that is incorporated into the solid cosmetic composition of the present invention has a mean particle size of 0.1–200 μm, preferably 0.5–20.0. When the particle size is less than 0.1 μm, a smooth plication sensation disadvantageously disappears, whereas when the particle size is in excess of 200 μm, the powder causes an unfavorable rough sensation when applied by rubbing.

The spherical powder of organopolysiloxane elastomer which is incorporated into the solid cosmetic composition of the present invention may be a perfectly spherical powder or an oblate spherical powder. However, a perfect spherical powder is more preferable in that the composition containing the powder imparts a more favorable smoother application sensation.

No particular limitation is imposed on the method for producing the spherical powder (having a mean particle size of 0.1–200 μm) of organopolysiloxane elastomer having a JIS A hardness of 50–100, and the powder can generally be produced by use of a curable organopolysiloxane composition as a raw material. Examples of the curable organopolysiloxane composition include:

an addition-curable organopolysiloxane composition which is cured through addition reaction between a diorganopolysiloxane having a silicon-bonded hydrogen atom and an organopolysiloxane having a silicon-bonded lower alkenyl group such as a vinyl group conducted in the presence of a platinum catalyst;

a condensation-curable organopolysiloxane composition which is cured through dehydrogenation reaction between a diorganopolysiloxane having hydroxyl groups at both molecule ends and a diorganopolysiloxane having a silicon-bonded hydrogen atom conducted in the presence of an organotin compound;

a condensation-curable organopolysiloxane composition which is cured through condensation reaction, such as dehydration or removal of alcohol, oxime, amine, amide, carboxylic acid, ketone, etc., between a diorganopolysiloxane having hydroxyl groups at both molecule ends and hydrolyzable organosilanes conducted in the presence of an organotin compound or titanate;

a peroxide-curable organopolysiloxane composition which is cured by the application of heat in the presence of an organic peroxide catalyst; and a high-energy-ray-curable organopolysiloxane composition which is cured through radiation of γ-rays, UV-rays, or an electron beam.

Among these curable organopolysiloxane compositions, an addition-curable organopolysiloxane composition is preferred, in view of a high curing rate and homogeneity in curing. A particularly preferable composition comprises (A) a diorganopolysiloxane having at least two silicon-bonded hydrogen atoms in the molecule; (B) an organopolysiloxane having at least two lower alkenyl groups in the molecule; and (C) a platinum catalyst.

An organic group other than a lower alkenyl group may also bond to a silicon atom in an organopolysiloxane or a diorganopolysiloxane serving as a predominant component of the above-mentioned curable organopolysiloxane composition, and examples of such an organic group include an alkyl group such as methyl, ethyl, propyl, butyl, or octyl; a substituted alkyl group such as 2-phenylethyl, 2-phenylpropyl, or 3,3,3-trifluoropropyl; an aryl group such as phenyl, tolyl, or xylyl; and a monovalent hydrocarbyl group having a substituent such as an epoxy, carboxylate, or mercapto group.

Several methods may be employed for producing the spherical powder (having a mean particle size of 0.1–200 µm) of organopolysiloxane elastomer having a JIS A hardness of 50–100 from the above-mentioned curable organopolysiloxane composition. Examples of the methods include the following (1) to (4):

(1) a method which involves mixing an addition-curable, condensation-curable, or peroxide-curable organopolysiloxane composition with water in the presence of a surfactant such as a nonionic, anionic, cationic, or amphoteric surfactant; forming a homogeneous aqueous dispersion by use of an apparatus such as a homogenization mixer, a colloid mill, a homogenizer, or a propeller mixer; releasing the dispersion into hot water at 50° C. or higher to thereby perform curing; and drying, (2) a method which involves spraying an addition-curable, condensation-curable, or peroxide-curable organopolysiloxane composition directly into hot airflow to thereby perform curing, (3) a method which involves spraying a high-energy-ray-curable organopolysiloxane composition under exposure to high-energy rays to thereby perform curing, and (4) a method which involves curing an addition-curable, condensation-curable, peroxide-curable, or high-energy-ray-curable organopolysiloxane composition and crushing the cured product by use of a known crushing apparatus such as a ball mill, an atomizer, a kneader, or a roll mill.

Of these, the method (1) is preferred in that a powder having a more spherical particle shape and a small variation in particle size can be produced.

A spherical powder of organopolysiloxane elastomer is described in detail in Japanese Patent Application Laid-Open (kokai) No. 2-243612 and Japanese Patent Publication (kokoku) Nos. 4-17162 and 4-66446. Commercial products may be incorporated into the solid cosmetic composition of the present invention, and examples of such products include Trefil E-505 and Trefil E-506C (products of Dow Corning Toray Silicone Co., Ltd.).

The solid cosmetic composition of the present invention contains the above-described spherical powder of organopolysiloxane elastomer in an amount of preferably 0.1–50.0 wt. % based on the entirety of the composition, particularly preferably 1.0–20.0 wt. %. When the content is less than 0.1 wt. %, an intended effect on improvement in use-related characteristics provided through incorporation of a spherical powder of organopolysiloxane elastomer, such as imparting a light and smooth application sensation, is poor, whereas when the content is in excess of 50.0 wt. %, the resultant solid cosmetic composition has poor strength against impact; disadvantageously exhibits sluggish spreadability on the skin; and imparts a rough sensation.

In addition to the above-described spherical powder of organopolysiloxane elastomer, a pigment powder may be incorporated into the solid cosmetic composition of the present invention. No particular limitation is imposed on the pigment powder so long as it is one that is typically incorporated into a cosmetic composition, and any pigment powder such as an inorganic pigment powder or an organic pigment powder may be incorporated.

Example of the inorganic pigments include talc, kaolin, calcium carbonate, zinc flower, titanium dioxide, red iron oxide, yellow iron oxide, black iron oxide, ultramarine, titanium-coated mica, bismuth oxychloride, a binderg pigment, ultramarine pink, hydrated chromium oxide, titanated mica, chromium oxide, cobalt aluminum oxide, iron blue, carbon black, silicic anhydride, magnesium silicate, bentonite, mica, sericite, zirconium oxide, magnesium oxide, zinc oxide, titanium oxide, precipitated calcium carbonate, heavy calcium carbonate, light magnesium carbonate, heavy magnesium carbonate, and calamine.

Examples of the organic pigments include polyester, polymethylmethacrylate, cellulose, Nylon-12, Nylon-6, styrene-acrylic acid copolymers, polypropylene, poly(vinyl chloride), nylon powder, polyethylene powder, benzoguanamine powder, tetrafluoroethylene powder, boron nitride, fish scale flake, lake tar pigments, lake natural pigments, and inorganic-organic hybrid pigments.

Preferably, the pigment powder is hydrophobicized. No particular limitation is imposed on the hydrophobicized pigment powder so long as the powder has a hydrophobic surface. Examples of such powders include a pigment powder surface-treated with high-viscosity silicone; a pigment powder coated with a silicone resin which has been preliminary reacted with alkyl hydrogen polysiloxane; silicone-coated powder further treated with alkene; a pigment powder treated with one or more surfactants selected from a cationic surfactant, an anionic surfactant, and a nonionic surfactant; a wax-coated pigment powder; a pigment powder treated with dextrinized fatty acid; and a pigment powder treated with a fluorine compound containing a perfluoroalkyl group.

The solid cosmetic composition of the present invention preferably contains powders including the above-described spherical powder of organopolysiloxane elastomer in an amount of 70.0–99.0 wt. % based on the entirety of the composition.

In addition to powders including the above-described spherical powder of organopolysiloxane elastomer, one or more ingredients which are typically added to a solid cosmetic composition, such as an oily ingredient or water, may be incorporated into the solid cosmetic composition of the present invention without impairing the effects of the present invention.

Examples of the oily ingredient which is incorporated into the solid cosmetic composition of the present invention include:

silicone oils such as dimethylpolysiloxane, dimethylcyclopolysiloxane, methylphenyl polysiloxane, methyl hydrogen polysiloxane, higher fatty acid-modified organopolysiloxane, higher alcohol-modified organopolysiloxane, trimethylsiloxysilicate, and decamethylcyclopentanesiloxane;

hydrocarbon oils such as liquid paraffin, squalane, vaseline, polyisobutylene, and microcrystalline wax;

ester oils such as isopropyl myristate, myristyl octyldodecanol, and di(2-ethylhexyl) succinate;

glycerides such as neopentyl glycol diisooctanoate, glyceryl monostearate, triglyceryl monoisostearate, and triglyceryl cocoate;

oils and fats such as castor oil and olive oil;

lower alcohols such as ethanol;

higher alcohols such as octyldodecanol, hexadecyl alcohol, cetyl alcohol, oleyl alcohol, stearyl alcohol, and polyethylene glycol;

higher fatty acids such as lauric acid, palmitic acid, oleic acid, stearic acid, and isostearic acid;

waxes such as lanolin and beeswax; and fluorocarbon oils.

Such oily ingredients are preferably incorporated in an amount of 1.0–30.0 wt. % based on the entirety of the composition.

When the solid cosmetic composition of the present invention is emulsified, the water content of the composition is typically 1.0–50.0 wt. % based on the entirety of the composition.

Other additives may also be incorporated into the solid cosmetic composition of the present invention, so long as the effects of the present invention are not impaired.

Examples of such additives include humectants such as polyhydric alcohol (e.g., glycerin), mucopolysaccharides (e.g., sodium hyaluronate), and organic acids and salts thereof (e.g., amino acids, amino acid salts, and hydroxy acid salts);

surfactants such as cationic surfactants, anionic surfactants, and nonionic surfactants;

pharmaceuticals such as vitamin E and vitamin E acetate;

astringents; antioxidants; preservatives; perfume; pH regulators such as sodium secondary phosphate; clay minerals; thickeners; and ultraviolet absorbents.

Of these, a humectant is preferably incorporated into the composition in order to prevent evaporation of water from the solid cosmetic composition per se.

The solid cosmetic composition of the present invention may be employed as foundation, face powder, cheek rouge, eye-shadow, eyebrow pencils, and eye-liner.

Specific formulations of the solid cosmetic composition of the present invention are described below.

EXAMPLES

The present invention is described in more detail by way of examples, which should not be construed as limiting the invention thereto.

Throughout the examples, unless otherwise stated, the amount of an incorporated ingredient represents weight % with respect to the entirety of the composition containing the ingredient.

JIS A hardness of an organopolysiloxane elastomer and the mean particle size of a spherical powder of organopolysiloxane elastomer were measured by the following methods. In addition, a sensory test and an impact resistance test of the cosmetic composition containing the powder was performed as described below.

<JIS A Hardness of Organopolysiloxane Elastomer>

An organopolysiloxane composition serving as a raw material was heated in a convection oven at 150° C. for one hour, to thereby prepare an organopolysiloxane elastomer. After the elastomer was cooled to room temperature, JIS A hardness of the elastomer was measured by use of a JIS A hardness meter specified by JIS K 6301.

<Mean Particle Size of Spherical Powder of Organopolysiloxane Elastomer>

Particles were observed under an optical microscope in order to measure the sizes thereof, and a mean value was calculated.

<Sensory Test>

A sensory test of the cosmetic composition was performed by a panel of 10 cosmetic experts in terms of the following five items: (1) spreadability, (2) light application sensation, (3) skin fittability, and (4) cosmetic retention. Regarding each item, in the case where 8 or more panelists evaluated the item as "good," a rating AA was given; in the case where 6–7 panelists evaluated the item as "good," a rating BB was given; in the case where 4–5 panelists evaluated the item as "good," a rating CC was given; and in the case where 3 or fewer panelists evaluated the item as "good," a rating DD was given.

Cosmetic retention of the cosmetic composition was evaluated by observation of the degree of make-up deterioration after a practical test during which subjects walked for two hours. "Good cosmetic retention" refers to the case where little or no deterioration of the makeup was visually observed by the panelist and the makeup remained mostly intact on the skin.

<Method of Impact Resistance Test>

A solid cosmetic composition was compression-molded into an inner dish. The compressed composition as contained in the dish was repeatedly dropped from a height of 50 cm onto an iron plate in order to evaluate impact resistance thereof. In the case where the composition was broken by 11 or more repetitions of dropping, a rating AA was given; in the case where the composition was broken by 7–10 repetitions of dropping, a rating BB was given; in the case where the composition was broken by 5–6 repetitions of dropping, a rating CC was given; and in the case where the composition was broken by 1–4 repetitions of droppings, a rating DD was given.

Examples 1 to 2 and Comparative Examples 1 to 5

A pressed powder containing the following ingredients was prepared in accordance with the method described below. The powder was subjected to a sensory test and an impact resistance test, and the results are shown in Table 1 along with the type of powder (7) employed.

The powders A through E shown in Table 1 are spherical powders of organopolysiloxane elastomer, and a method for producing these powders is described hereinbelow. Powder F represents a polymethylsilsesquioxane powder, which is commercially available under the name Tospearl (product of Toshiba Silicone Co., Ltd.). Respective powders were subjected to measurement of JIS A hardness and mean particle size. The results are shown in Table 2.

| Ingredient | Amount (wt. %) |
|---|---|
| (1) talc | balance |
| (2) sericite | 10.0 |
| (3) kaolin | 5.0 |
| (4) titanium dioxide | 5.0 |
| (5) zinc myristate | 5.0 |
| (6) color pigment | 3.0 |
| (7) powder | 10.0 |
| (8) porous spherical silica (mean particle size: 3 μm) | 5.0 |
| (9) squalane | 3.0 |
| (10) glyceryl triisooctanoate | 2.0 |
| (11) preservative | suitable amount |
| (12) perfume | suitable amount |

<Method of Production>

Ingredients (1) and (6) were blended by use of a blender. Ingredients (2) to (5), (7), and (8) were added to the mixture, and the resultant mixture was further mixed sufficiently. Ingredients (9) to (11) were added to the resultant mixture. After the color of the mixture was adjusted, ingredient (12) was sprayed thereto and the resultant mixture was homogenized. Subsequently, the mixture was crushed by use of a crusher, passed through a sieve, and compression-molded into an inner dish, to thereby obtain a pressed powder.

TABLE 1

|  | Example | | Comparative Example | | | | |
| --- | --- | --- | --- | --- | --- | --- | --- |
|  | 1 | 2 | 1 | 2 | 3 | 4 | 5 |
| Powder used as ingredient (7) | A | B | none | C | D | E | F |
| Sensory test |  |  |  |  |  |  |  |
| 1. Spreadability | AA | BB | DD | CC | DD | DD | DD |
| 2. Light application sensation | AA | BB | DD | CC | CC | CC | DD |
| 3. Skin fittability | AA | CC | DD | DD | BB | BB | DD |
| 4. Cosmetic retention | AA | BB | DD | BB | BB | BB | DD |
| Impact resistance | AA | AA | DD | DD | DD | DD | DD |

As is apparent from Table 1, as compared with the cases of Comparative Examples 1 to 5, the pressed powders of Examples 1 and 2, which contain a spherical powder of organopolysiloxane elastomer having a JIS A hardness of 50–100 (the mean particle size of the powder is 0.1–200 μm), exhibit high impact resistance and were not rated "DD" in terms of any of the evaluation items (1) to (4) in the above-described sensory test, even though the tested pressed powders contain a relatively large amount of the spherical powder of organopolysiloxane elastomer (10 wt. %). Thus, the pressed powders of Examples 1 and 2 are more excellent in overall evaluation than are pressed powders of Comparative Examples 1 to 5.

Method for Producing Spherical Powder of Organopolysiloxane Elastomer (Powder A)

Polydimethylsiloxane having dimethylvinylsiloxy groups at both ends of the molecular chain (vinyl equivalent=2500) (100 parts by weight), polymethylhydrogensiloxane having trimethylsiloxy groups at both ends of the molecular chain (viscosity: 20 mPa·s) (5.2 parts by weight), and an isopropanol solution containing platinic chloride (an amount as reduced to 50 ppm of platinum with respect to the entirety of the resultant composition) were homogeneously blended at 5° C., to thereby prepare a liquid organopolysiloxane composition.

This liquid organopolysiloxane composition was quickly mixed into an aqueous solution (300 parts by weight) containing pure water (electric conductivity: 0.2 μS/cm) and 2 wt. % of polyoxyethylene (9 mol-added) lauryl ether at 25° C. Subsequently, the resultant mixture was treated by use of a homogenizer (300 kgf/cm²), to thereby prepare an aqueous dispersion in which a liquid organopolysiloxane composition was homogeneously dispersed.

The resultant aqueous dispersion was allowed to stand at 30° C. for 6 hours, and then heated at 80° C. for 1 hour, to thereby cure the composition. Subsequently, the aqueous dispersion was dried by use of a spray dryer, to thereby obtain a spherical powder of organopolysiloxane elastomer (powder A).

Method for Producing Spherical Powder of Organopolysiloxane Elastomer (Powder B)

Polydimethylsiloxane having dimethylvinylsiloxy groups at both ends of the molecular chain (vinyl equivalent=2500) (100 parts by weight), polymethylhydrogensiloxane having trimethylsiloxy groups at both ends of the molecular chain (viscosity: 20 mPa·s) (5.2 parts by weight), and an isopropanol solution containing platinic chloride (an amount as reduced to 50 ppm of platinum with respect to the entirety of the resultant composition) were homogeneously blended at 5° C., to thereby prepare a liquid organopolysiloxane composition.

This liquid organopolysiloxane composition was quickly mixed into an aqueous solution (300 parts by weight) containing pure water (electric conductivity: 0.2 μS/cm) and 2 wt. % of polyoxyethylene (9 mol-added) lauryl ether at 25° C. Subsequently, the resultant mixture was treated by use of a homogenizer (200 kgf/cm²), to thereby prepare an aqueous dispersion in which a liquid organopolysiloxane composition was homogeneously dispersed.

The resultant water dispersion was allowed to stand at 30° C. for 6 hours, and then heated at 80° C. for 1 hour, to thereby cure the composition. Subsequently, the aqueous dispersion was dried by use of a spray dryer, to thereby obtain a spherical powder of organopolysiloxane elastomer (powder B).

Method for Producing Spherical Powder of Organopolysiloxane Elastomer (Powder C)

Polydimethylsiloxane having dimethylvinylsiloxy groups at both ends of the molecular chain (vinyl equivalent=2500) (100 parts by weight), polymethylhydrogensiloxane having trimethylsiloxy groups at both ends of the molecular chain (viscosity: 20 mPa·s) (5.2 parts by weight), and an isopropanol solution containing platinic chloride (an amount as reduced to 50 ppm of platinum with respect to the entirety of the resultant composition) were homogeneously blended at 5° C., to thereby prepare a liquid organopolysiloxane composition.

This liquid organopolysiloxane composition was quickly mixed into an aqueous solution (300 parts by weight) containing pure water (electric conductivity: 0.2 μS/cm) and 2 wt. % of polyoxyethylene (9 mol-added) lauryl ether at 25° C. Subsequently, the resultant mixture was treated by use of a homogenizer (100 kgf/cm²), to thereby prepare an aqueous dispersion in which a liquid organopolysiloxane composition was homogeneously dispersed.

The resultant aqueous dispersion was allowed to stand at 30° C. for 6 hours, and then heated at 80° C. for 1 hour, to thereby cure the composition. Subsequently, the aqueous dispersion was dried by use of a spray dryer, to thereby obtain a spherical powder of organopolysiloxane elastomer (powder C).

Method for Producing Spherical Powder of Organopolysiloxane Elastomer (Powder D)

Polydimethylsiloxane having dimethylvinylsiloxy groups at both ends of the molecular chain (vinyl equivalent=5000) (100 parts by weight), dimethylsiloxane·methylhydrogensiloxane copolymer having trimethylsiloxy groups at both ends of the molecular chain (4.5 parts by weight), dimethylpolysiloxane having trimethylsiloxy groups at both ends of the molecular chain (viscosity: 100 cSt) (50 parts by weight), and an isopropanol solution containing platinic chloride (an amount as reduced to 50 ppm of platinum with respect to the entirety of the resultant composition) were homogeneously blended at 5° C., to thereby prepare a liquid organopolysiloxane composition.

This liquid organopolysiloxane composition was quickly mixed into an aqueous solution (300 parts by weight) containing pure water (electric conductivity: 0.2 μS/cm) and 2 wt. % of polyoxyethylene (9 mol-added) lauryl ether at 25°

C. Subsequently, the resultant mixture was treated by use of a homogenizer (300 kgf/cm²), to thereby prepare an aqueous dispersion in which a liquid organopolysiloxane composition was homogeneously dispersed.

The resultant aqueous dispersion was allowed to stand at 30° C. for 6 hours, and then heated at 80° C. for 1 hour, to thereby cure the composition. Subsequently, the aqueous dispersion was dried by use of a spray dryer, to thereby obtain a spherical powder of organopolysiloxane elastomer (powder D).

Method for Producing Spherical Powder of Organopolysiloxane Elastomer (Powder E)

Polydimethylsiloxane having dimethylvinylsiloxy groups at both ends of the molecular chain (vinyl equivalent=5000) (100 parts by weight), dimethylsiloxane-methylhydrogensiloxane copolymer having trimethylsiloxy groups at both ends of the molecular chain (4.5 parts by weight), and an isopropanol solution containing platinic chloride (an amount as reduced to 50 ppm of platinum with respect to the entirety of the resultant composition) were homogeneously blended at 5° C., to thereby prepare a liquid organopolysiloxane composition.

This liquid organopolysiloxane composition was quickly mixed into an aqueous solution (300 parts by weight) containing pure water (electric conductivity: 0.2 µS/cm) and 2 wt. % of polyoxyethylene (9 mol-added) lauryl ether at 25° C. Subsequently, the resultant mixture was treated by use of a homogenizer (300 kgf/cm²), to thereby prepare an aqueous dispersion in which a liquid organopolysiloxane composition was homogeneously dispersed.

The resultant aqueous dispersion was allowed to stand at 30° C. for 6 hours, and then heated at 80° C. for 1 hour, to thereby cure the composition. Subsequently, the aqueous dispersion was dried by use of a spray dryer, to thereby obtain a spherical powder of organopolysiloxane elastomer (powder E).

TABLE 2

| Powder | A | B | C | D | E | F |
|---|---|---|---|---|---|---|
| Mean particle size (µm) | 4 | 50 | 250 | 5 | 3 | 3 |
| JIS A hardness | 60 | 80 | 70 | 30 | 40 | 90 or more |

Further examples of the solid cosmetic composition of the present invention—Examples 3 to 5 and Comparative Examples 6 to 9—are described below. Each solid cosmetic composition was subjected to the above-described sensory test (items (1)–(4)) and impact resistance test. The results are shown in Table 3, along with the results of the sensory test and impact resistance test of the pressed powder in Example 1.

Example 3

Powdery Foundation

| Ingredient | Amount (wt. %) |
|---|---|
| (1) talc | balance |
| (2) sericite | 15.0 |
| (3) mica | 20.0 |

-continued

| Ingredient | Amount (wt. %) |
|---|---|
| (4) titanium dioxide | 10.0 |
| (5) color pigment | 5.0 |
| (6) spherical powder of organopolysiloxane elastomer (powder B) | 5.0 |
| (7) spherical resin powder ("Microsponge," product of Dow Corning Toray Co., Ltd.; mean particle size: 7 µm) | 10.0 |
| (8) squalane | 6.0 |
| (9) dimethylpolysiloxane | 3.0 |
| (10) octyl myristate | 3.0 |
| (11) sorbitan monooleate | 1.0 |
| (12) preservative, antioxidant | suitable amount |
| (13) perfume | suitable amount |

<Method of Production>

The ingredients were mixed in the same manner as described in Example 1, to thereby obtain a powdery foundation.

Example 4

Two-way Foundation

| Ingredient | Amount (wt. %) |
|---|---|
| (1) silicone-treated talc | balance |
| (2) silicone-treated mica | 20.0 |
| (3) silicone-treated titanium dioxide | 10.0 |
| (4) silicone-treated color pigment | 5.0 |
| (5) spherical powder of organopolysiloxane elastomer (powder A) | 20.0 |
| (6) porous plate-shaped silica (mean particle size: 4 µm) | 15.0 |
| (7) solid paraffin | 1.0 |
| (8) liquid paraffin | 6.0 |
| (9) dimethylpolysiloxane | 4.0 |
| (10) octyl methoxycinnamate | 2.0 |
| (11) preservative, antioxidant | suitable amount |
| (12) perfume | suitable amount |

<Method of Production>

The ingredients were mixed in the same manner as described in Example 1, to thereby obtain a two-way (i.e., usable with or without water) foundation.

Example 5

Powdery Foundation

| Ingredient | Amount (wt. %) |
|---|---|
| (1) talc | balance |
| (2) sericite | 10.0 |
| (3) mica | 5.0 |
| (4) titanium dioxide | 10.0 |
| (5) color pigment | 5.0 |
| (6) spherical powder of organopolysiloxane elastomer (powder A) | 5.0 |
| (7) porous spherical silica (mean particle size: 5 µm) | 35.0 |
| (8) squalane | 6.0 |
| (9) dimethylpolysiloxane | 3.0 |
| (10) octyl myristate | 3.0 |

-continued

| Ingredient | Amount (wt. %) |
|---|---|
| (11) sorbitan monooleate | 1.0 |
| (12) preservative, antioxidant | suitable amount |
| (13) perfume | suitable amount |

<Method of Preparation>

The ingredients were mixed in the same manner as described in Example 1, to thereby obtain a powdery foundation.

Comparative Example 6

The procedure of Example 1 was repeated except that the spherical powder of organopolysiloxane elastomer was replaced by talc, to thereby obtain a pressed powder.

Comparative Example 7

The procedure of Example 3 was repeated except that the spherical powder of organopolysiloxane elastomer was replaced by talc, to thereby obtain a powdery foundation.

Comparative Example 8

The procedure of Example 4 was repeated except that the spherical powder of organopolysiloxane elastomer was replaced by silicone-treated talc, to thereby obtain a two-way foundation.

Comparative Example 9

The procedure of Example 5 was repeated except that the spherical powder of organopolysiloxane elastomer was replaced by talc, to thereby obtain a powdery foundation.

TABLE 3

|  | Spread-ability | Light Application sensation | Skin fittability | Cosmetic retention | Impact resistance |
|---|---|---|---|---|---|
| Example 1 | AA | AA | AA | AA | AA |
| Example 3 | AA | BB | BB | BB | AA |
| Example 4 | AA | BB | AA | AA | AA |
| Example 5 | AA | AA | AA | AA | AA |
| Comparative Example 6 | CC | CC | CC | CC | CC |
| Comparative Example 7 | CC | CC | CC | CC | CC |
| Comparative Example 8 | CC | CC | CC | CC | DD |
| Comparative Example 9 | CC | CC | CC | CC | DD |

As is clear from Table 3, the cosmetic compositions of Example 1 and Examples 3–5 are superior to the cosmetic compositions of Comparative Examples 6–9 in terms of impact resistance, spreadability, light application sensation, skin fittability, and cosmetic retention.

What is claimed is:

1. A method of producing an impact resistant solid cosmetic, said method comprising compression molding into a dish mold powder materials comprising spherical powder of organopolysiloxane elastomer having a JIS A hardness of 60–100, and a mean particle size of 0.1–200 mm, said elastomer constituting 0.1–50.0 wt % based on the entirety of the cosmetic.

2. The method according to claim 1, wherein the powder materials are compression molded at a pressure of between 200 kgf/cm$^2$ and 300 kgf/cm$^2$.

3. The method according to claim 1, wherein the powder materials are compression molded at a temperature of between 10° C. and 30° C.

4. The method according to claim 1, wherein the compacted powder materials in the compacted cosmetic constitutes 70.0–99.0 wt %, based on the entirety of the cosmetic.

5. The method according to claim 1, wherein the impact resistant solid cosmetic further comprises an oily ingredient.

6. The method according to claim 5, wherein the amount of the oily ingredient is 1.0–30.0 wt %.

7. The method according to claim 1, wherein the organopolysiloxane elastomer has a JIS A hardness of 60–80.

8. The method according to claim 1, wherein the cosmetic is selected from the group consisting of face powder, powdery foundation, two way foundation, formulations usable with water, solid emulsified formulation, and cheek rouge.

9. A method of producing an impact resistant solid cosmetic comprising compacted powder materials, said method comprising compression molding into a dish mold a mixture comprising 70.0–99.0 wt % of said powder materials and 1.0–30.0 wt % of an oily ingredient, said powder materials comprising a spherical powder of organopolysiloxane elastomer having a JIS A hardness of 60–100, and a mean particle size of 0.1–200 mm, said elastomer constituting 0.1–50.0 wt % based on the entirety of the cosmetic.

10. The method according to claim 9, wherein the powder materials are compression molded at a pressure of between 200 kgf/cm$^2$ and 300 kgf/cm$^2$ at a temperature of between 10° C. and 30° C.

11. The method according to claim 1, wherein the powder materials are compacted 1–3 times.

12. The method of claim 11, wherein the powder materials are compacted at a temperature of about 20° C.±10° C.

13. The method of claim 12, wherein the powder materials are compacted under a pressure of 200–300 kgf/cm$^2$.

14. An impact resistant solid cosmetic produced by the method of claim 1.

15. An impact resistant solid cosmetic produced by the method of claim 5.

16. An impact resistant solid cosmetic produced by the method of claim 9.

17. An impact resistant solid cosmetic produced by the method of claim 10.

18. An impact resistant solid cosmetic produced by the method of claim 13.

* * * * *